United States Patent
VanWiggeren

(10) Patent No.: US 7,474,404 B2
(45) Date of Patent: Jan. 6, 2009

(54) VOLTAGE SENSOR CAPABLE OF CONTACTLESS VOLTAGE MEASUREMENT

(75) Inventor: Gregory D. VanWiggeren, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 88 days.

(21) Appl. No.: 11/741,567

(22) Filed: Apr. 27, 2007

(65) Prior Publication Data

US 2008/0266568 A1    Oct. 30, 2008

(51) Int. Cl.
*G01N 21/55* (2006.01)
(52) U.S. Cl. ........................... 356/445; 356/447
(58) Field of Classification Search ............. 422/55–58, 422/82.05; 356/335–344, 436–442, 445
See application file for complete search history.

(56) References Cited

U.S. PATENT DOCUMENTS

| | | | | |
|---|---|---|---|---|
| 4,844,613 | A | * | 7/1989 | Batchelder et al. .......... 356/318 |
| 5,451,980 | A | * | 9/1995 | Simon et al. .................. 345/88 |
| 6,956,221 | B2 | * | 10/2005 | Gruhlke .................... 250/458.1 |

* cited by examiner

*Primary Examiner*—L. G Lauchman
*Assistant Examiner*—Jarreas C Underwood
(74) *Attorney, Agent, or Firm*—Ian Hardcastle

(57) ABSTRACT

A voltage sensor capable of single-point or simultaneous multi-point contactless voltage measurement has an electro-optic transducer, a surface plasmon resonance (SPR) and an optical system. The electro-optic transducer is operable to translate an electric field dependent on the voltage in a device under test field to a variation in refractive index. The surface plasmon resonance (SPR) transducer is juxtaposed with the electro-optic transducer and is operable to translate the variation in the refractive index of the electro-optic transducer to a variation in reflectivity. The optical system is configured to illuminate the SPR transducer with incident light at a surface plasmon resonance-inducing angle of incidence and to detect light reflected by the SPR transducer at a single point or at multiple points within a region.

18 Claims, 4 Drawing Sheets

VOLTAGE SENSOR CAPABLE OF CONTACTLESS VOLTAGE MEASUREMENT

BACKGROUND

People measure voltages for many reasons. Typical electronic test equipment measures a voltage at a point within some environment of interest by directly contacting the point with a probe. Examples of such equipment include AC and DC voltmeters, oscilloscopes and many types of RF test equipment, especially if the concept of "probing" includes propagating electromagnetic energy inducing a voltage in a suitable antenna. Such measurements are the stock-in-trade of those engaged in designing, developing and testing electrical devices, including diagnosing and repairing such devices.

In many voltage measurement applications, it is practical to make a voltage measurement through physical contact of a probe with a conductor. However, there are cases where contactless measurements are highly desirable, if not absolutely necessary. Typically, a contactless measurement is needed when the conductor whose voltage is to be measured does not have an exposed portion that can be contacted. For example, conductors that are on the inner layers of a multi-layer printed circuit board, e.g., transmission lines, do not have such exposed portion. Ball grid arrays are another example.

Another example is the conductors of a flat-panel display (FPD) that, for example, constitutes part of a computer monitor or a large-format, high-definition television and that has been fabricated to a point at which the conductors have been encapsulated and can no longer be contacted with a probe. Even if they are not yet encapsulated, the conductors are microscopic and fragile. Even when the test is performed at a point in the manufacturing process before the conductors are enclosed by a protective covering, the number of locations to be probed is large, and each location is delicate and can easily be damaged by contact with a probe. To obtain a reasonable test throughput, possibly thousands of measurement locations have to be probed simultaneously. Each location is distanced from its neighboring locations by the pitch of the display, which is typically a few hundred micrometers. A suitable multi-probe probe head is typically expensive and its use incurs the risk that a probe will damage the flat-panel display under test, resulting in a failure either instantly or some future time. The cost of such a probe head and the cost of damaged units contribute significantly to the cost of flat-panel displays.

Non-contact voltage measurement techniques that discover the presence of a voltage on a conductor include those based on the Pockels effect and involve measuring the effect of an electric field on the polarization of light passing through an optically-transmissive medium located in the electric field. While this technique has its advantages, it fails to provide an adequate sensitivity and spatial resolution. Another non-contact voltage measurement technique involves scanning the device under test with an electron beam to detect the emission of secondary electrons. This test technique has a better voltage sensitivity and spatial resolution, but it is performed in a high vacuum, which significantly increases the test time.

What is needed, therefore, is a voltage measurement technique that is capable of contactless voltage measurement and that has a voltage sensitivity, spatial resolution and operational convenience suitable for rapidly measuring voltage at multiple, small measurement locations in a device under test. What is also needed is a voltage measurement technique that can be used to make simultaneous contactless voltage measurements in a relatively large area of a device under test.

DETAILED DESCRIPTION

Figure 1:
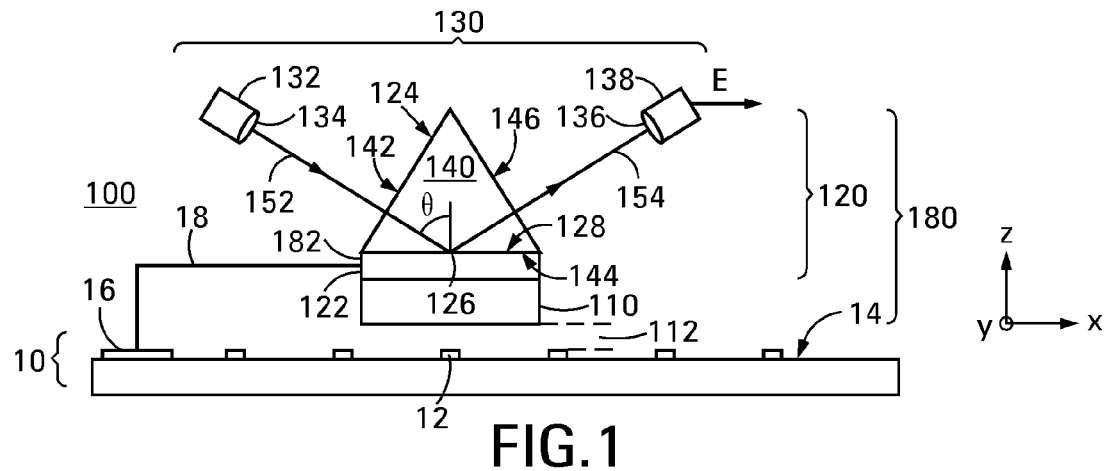
FIG. 1 is a schematic side view showing an example of a voltage sensor in accordance with an embodiment of the invention capable of contactlessly measuring a voltage in a device under test.

A voltage sensor in accordance with an embodiment of the invention is capable of contactlessly measuring a voltage in a device under test. The voltage sensor is aligned with a measurement location in the device under test whose voltage is to be measured but is not in physical or electrical contact with the measurement location. The voltage sensor employs an electro-optic transducer juxtaposed with a surface plasmon resonance (SPR) transducer to modulate the intensity of light in response to an electric field that depends on the voltage at the measurement location. By measuring the intensity of the light, the voltage at the measurement location can be determined.

Aligning the voltage sensor with the measurement location in the device under test subjects the electro-optic transducer to an electric field that depends on the voltage at the measurement location. The electro-optic transducer translates the electric field to a corresponding variation in its refractive index. The SPR transducer juxtaposed with the electro-optic transducer translates the variation in the refractive index of the electro-optic transducer to a corresponding variation in its reflectivity. An optical system illuminates the SPR transducer at an angle of incidence that induces surface plasmon resonance in the SPR transducer and detects the light reflected by the SPR transducer. Detecting the reflected light generates an electrical signal that represents the voltage at the measurement location.

A voltage sensor in accordance with another embodiment of the invention is capable of contactlessly measuring a spatial voltage variation in a device under test or in a region of the device under test. Such voltage sensor is capable of making multiple voltage measurements simultaneously. The voltage sensor is aligned with a region of the device under test where voltages are to be measured but is not in physical or electrical contact with the device under test. The voltage sensor employs an electro-optic transducer juxtaposed with a surface plasmon resonance (SPR) transducer to spatially modulate the intensity of light in response to an electric field having a spatial variation that depends on the spatial voltage variation in the device under test. By forming an image of the SPR sensor using the reflected light and measuring the intensity of the light at multiple points within the image, the voltages at multiple measurement locations in the device under test can be determined.

Aligning the voltage sensor with the device under test subjects the electro-optic transducer to an electric field having a spatial variation that depends on the spatial voltage variation in the device under test. The electro-optic transducer translates the spatial variation in the electric field to a corresponding spatial variation in its refractive index. The SPR transducer juxtaposed with the electro-optic transducer translates the spatial variation in the refractive index of the electro-optic transducer to a corresponding spatial variation in its reflectivity. An optical system illuminates the SPR transducer at an angle of incidence that induces surface plasmon resonance in the SPR transducer and forms an image on an array of light detectors using the light reflected by the SPR transducer. Detecting the reflected light using the array of light detectors generates an electrical signal that represents the voltages at the measurement locations.

In a voltage sensor in accordance with an embodiment of the invention, the SPR transducer uses surface plasmon resonance to translate the variation of the refractive index of the electro-optic transducer to a variation in its reflectivity. The SPR transducer is composed of a resonant layer structure and a transparent body through which the optical system illuminates the resonant layer structure. The transparent body is composed of a material having a refractive index greater than that of air.

What will be called an SPR layer constitutes at least part of the resonant layer structure. The SPR layer is a layer in which light having an appropriate wavelength and an appropriate angle of incidence will induce surface plasmon resonance. In some examples, the SPR layer is a single thin layer of a metal. In other examples, SPR layer is composed of thin layers of more than one material, such as alternating layers of two different metals or alternating layers of dielectric and metal. In the SPR layer, the metal layer or layers each have a thickness of the order of tens of nanometers, and the dielectric layer or layers, if present, each have a thickness of the order of hundreds of nanometers. In some examples, the SPR layer constitutes the entire resonant layer structure. In other examples, the resonant layer structure is composed of an SPR layer and a thicker dielectric layer juxtaposed with the SPR layer such that the SPR layer is exposed to the incident light.

When the resonant layer structure is illuminated through the transparent body with a beam of nominally monochromatic incident light, the resonant layer structure typically behaves as a mirror and reflects the incident light at an angle of reflection equal to the angle of incidence. Under these conditions, the resonant layer structure will be said to have a normal reflectivity. However, in a narrow range of the angle of incidence, the reflectivity of the resonant layer structure will fall below the normal reflectivity, and the intensity of the reflected light will fall as a result. At one special angle of incidence that will be called the SPR angle, the reflectivity of the resonant layer structure and, hence, the intensity of the reflected light, falls to a minimum. The SPR angle depends on the wavelength of the incident light, the refractive index of the transparent body, the material or materials of the resonant layer structure, and the refractive index of the electro-optic transducer.

References below to the SPR angle of an SPR transducer should be taken to refer to the SPR angle of the resonant layer structure of the SPR transducer. Similarly, references below to the reflectivity of an SPR transducer should be taken to refer to the reflectivity of the resonant layer structure of the SPR transducer. Finally, references herein to inducing surface plasmon resonance in an SPR transducer should be taken to refer to inducing surface plasmon resonance in the SPR layer of the resonant layer structure of the SPR transducer.

The intensity of the reflected light is reduced at the SPR angle because incident light induces surface plasmon resonance in the SPR layer of the resonant layer structure and the surface plasmon resonance absorbs the energy of the incident light. Specifically, when surface plasmon resonance is induced, the atomic structure of the SPR layer acts as an electron resonator coupled to the incident light. The electron resonator absorbs the energy of the incident light. At angles of incidence greater than and less than the SPR angle, the reflectivity of the resonant layer structure progressively increases towards the normal reflectivity with a characteristic similar to a typical Lorentzian resonance characteristic.

When incident light induces surface plasmon resonance in the resonant layer structure, electric fields called evanescent fields appear on the non-illuminated side of the resonant layer structure and extend from the non-illuminated side of the resonant layer structure. The evanescent fields have a physical size of about one half of the wavelength of the incident light. The refractive index of any material into which the evanescent fields extend has a significant effect on the SPR angle, i.e., the angle of incidence at which surface plasmon resonance occurs.

In a contactless voltage sensor in accordance with an embodiment of the invention, the SPR transducer is juxtaposed with the electro-optic transducer, so that the evanescent fields generated by surface plasmon resonance in the resonant layer structure of the SPR transducer extend into the electro-optic transducer. In typical examples, the electro-optic transducer is fabricated on the resonant layer structure. In other examples, one or more intervening layers may separate the electro-optic transducer from the SPR transducer provided that such intervening layers do not prevent the evanescent field from extending into the electro-optic transducer.

As a result of the evanescent field extending into the electro-optic transducer, the SPR angle of the SPR transducer depends on the refractive index of the electro-optic transducer. The refractive index of the electro-optic transducer in turn depends on the electric field to which the electro-optic transducer is subject, e.g., the electric field resulting from the voltage between the measurement location in the device under test and the voltage sensor. If, when the electro-optic transducer is not subject to an electric field, the angle of incidence is set to one that in turn sets the SPR transducer to a predetermined reflectivity, less than normal reflectivity, the reflectivity of the SPR transducer will differ from the predetermined reflectivity when the electro-optic transducer is subject to the electric field. This is because the electric field changes the refractive index of the electro-optic transducer, and the changed refractive index of the electro-optic transducer in turn changes the SPR angle of the SPR transducer. The change in the SPR angle changes the reflectivity of the SPR transducer at the fixed angle of incidence at which it is illuminated. As will be described in greater detail below, the intensity of the light reflected by the SPR transducer can be measured to obtain a measure of the voltage at the measurement location.

FIG. 1 is a schematic side view showing an example of a voltage sensor 100 in accordance with an embodiment of the invention capable of contactlessly measuring a voltage in a device under test. Voltage sensor 100 is composed of an electro-optic transducer 110, a surface plasmon resonance (SPR) transducer 120 and an optical system 130. Electro-optic transducer 110 is operable to translate an electric field dependent on a voltage in the device under test to a variation in its refractive index. SPR transducer 120 is juxtaposed with electro-optic transducer 110, and is operable to translate the variation in the refractive index of electro-optic transducer 110 to a variation in its reflectivity. Optical system 130 is configured to illuminate SPR transducer 120 with light at a surface plasmon resonance-inducing angle of incidence and to detect light reflected by the SPR transducer.

FIG. 1 shows voltage sensor 100 positioned to measure the voltage of a conductor 12 located on a major surface 14 of an exemplary device under test 10. In other devices under test, conductor 12 is beneath surface 14 and is covered by an insulating layer, which makes it impossible to contact conductor 12 with a conventional probe and also prevents physical contact between conductor 12 and voltage sensor 100. Voltage sensor 100 is aligned in the x- and y-directions shown in FIG. 1 such that the location 126 on SPR transducer 120 that is illuminated by incident light 152 from optical system 130 is aligned in the x-y plane with conductor 12 whose voltage sensor 100 is to measure. Voltage sensor 100 is also positioned in the z-direction shown in FIG. 1 such that the surface of electro-optic transducer 100 remote from SPR transducer 120 is separated from surface 14 by a narrow gap 112. As will be described below, reducing gap 112 increases the spatial resolution and voltage sensitivity of voltage sensor 100. However, gap 112 should be sufficiently wide to ensure that voltage sensor 100 will not collide with high spots on device under test 10 as it is moved in the x- and y-directions to perform voltage measurements at multiple measurement locations on device under test 10.

The voltage measurement performed by voltage sensor 100 is contactless only in the sense that it is made without physical contact between the voltage sensor and the measurement location in device under test 10 where a voltage is to be measured. Avoiding physical contact between the voltage sensor and the measurement location in the device under test minimizes risk of the voltage sensor damaging the device under test and allows the voltage sensor to measure the voltage at a measurement location that is inaccessible to a conventional probe. In applications in which physical contact between voltage sensor 100 and the device under test results in an acceptable risk of damage to the device under test, voltage sensor 100 is additionally capable of measuring a voltage in the device under test while in physical contact with the device under test.

Notwithstanding its contactless appellation, voltage sensor 100 is electrically connected to a voltage reference point 16 on device under test 10 by an electrical connection 18. Electrical connection 18 defines a voltage relationship between the voltage sensor and the device under test. The voltage relationship allows a voltage on device under test 10 to subject electro-optic transducer 110 to a defined electric field. Voltage reference point 16 is typically a robust and easily-accessible point on device under test 10, such as a signal ground or a power ground, to which electrical connection 18 can conveniently be made. In the example shown, electrical connection 18 is a direct electrical connection between voltage sensor 100 and voltage reference point 16. Alternatively, electrical connection 18 may be an indirect electrical connection between voltage sensor 100 and voltage reference point 16. For example, such indirect electrical connection may be made though a measurement apparatus (not shown) of which voltage sensor 100 constitutes part and that is connected to the voltage reference point 16 of device under test 10. In the example shown, the electrical connection to voltage sensor 100 is made at SPR transducer 120, specifically, to an electrically-conducting portion thereof, such as a metal SPR layer.

In voltage sensor 100, electro-optic transducer 110 comprises a layer of electro-optical material whose refractive index depends on an applied electric field. Typical electro-optical materials include polymers, and crystalline materials such as lithium niobate. However, such materials exhibit a relatively weak electro-optic effect compared with liquid crystal materials. Thus, electro-optic transducer 110 is typically a liquid crystal cell comprising a layer of liquid crystal material sandwiched between two spaced substrates. An orientation layer that defines the orientation of the liquid crystal material is typically interposed between the liquid crystal material and each substrate. Electro-optic transducer 110 will be described in greater detail below with reference to FIG. 3.

SPR transducer 120 comprises a resonant layer structure 122 and a transparent body 124 through which resonant layer structure 122 is illuminated. In the example shown, resonant layer structure 122 is composed of an SPR layer 182, and SPR layer 182 is a single layer of metal having a thickness of the order of tens of nanometers. In an example, SPR layer 182 was a single layer of gold about 45 nm thick. In other examples, SPR layer 182 is a single layer of another metal, such as silver or aluminum with a thickness of the order of tens of nanometers. As noted above, SPR layer 182 can alternatively be composed of multiple layers of metals or multiple layers of metals and dielectrics. For a given wavelength of incident light, the SPR angle of resonant layer structure 122 depends on the thickness and material(s) of SPR layer 182, the refractive index of transparent body 124 and the refractive index of electro-optic transducer 110. Illuminating SPR layer 182 through transparent body 124 decreases the wavelength of the incident light at the surface 128 of the SPR layer to one that will match, and therefore resonate with, the wavelength of the plasmons at the surface 128 of the SPR layer.

In the example shown, a triangular prism 140 provides transparent body 124 through which resonant layer structure 122 is illuminated. Prism 140 has faces 142, 144 and 146. In the example shown, SPR layer 182 constituting resonant layer structure 122 is deposited on face 144 of prism 140. Prism 140 is also structured to minimize reflection losses of incident light 152 and reflected light 154 as they pass through faces 142 and 146, respectively, of the prism. Prism 140 may alternatively be trapezoidal. Transparent body 124 may have other shapes, as will be described below with reference to FIG. 7.

In the example shown in FIG. 1, optical system 130 is composed of a laser 132 or other monochromatic or narrow-band light source, such as a light-emitting diode (LED), an auxiliary lens 134, an auxiliary lens 136 and a detector 138. Auxiliary lens 134 collimates light generated by laser 132 to form a narrow incident beam 152 that passes through faces 142 and 144 of prism 140 and is incident on location 126 on the surface 128 of SPR transducer 120 remote from electro-optic transducer 110. The beam cross-sectional size of incident light 152 depends on the size of the features, such as conductor 12, on device under test 10 whose voltages are to be measured. Incident beam 152 forms a spot at location 126 on surface 128 that is typically no larger in size than the features of device under test 10 whose voltages are to be measured. This prevents voltage sensor 100 from measuring the voltage of a nearby feature in addition to the voltage at the measurement location in device under test 10. A voltage sensor capable of contactlessly measuring voltages at multiple measurement locations will be described below with reference to FIG. 6. Auxiliary lens 134 may be unnecessary with some configurations of laser 132.

Laser 132 and auxiliary lens 134 are positioned relative to SPR transducer 120 such that incident light 152 illuminates surface 128 at an angle of incidence θ that induces surface plasmon resonance in SPR transducer 120. As will be described in more detail below, angle of incidence θ depends in part on the material(s) of resonant layer structure 122 and the wavelength of incident light 152 in the material of prism 140. Unless otherwise stated, all angles of incidence, reflection and refraction referred to in this disclosure are measured relative to the normal to the surface, e.g., surface 128, at which the reflection or refraction takes place.

The resonant layer structure 122 of SPR transducer 120 reflects incident light 152 as reflected light 154. Resonant layer structure 122 has a reflectivity that depends on the refractive index of electro-optic transducer 110. Reflected light 154 passes through face 146 of prism 140 to auxiliary lens 136 and detector 138. Auxiliary lens 136 focuses the reflected light on detector 138. Auxiliary lens 136 may be unnecessary with some configurations of detector 138. In response to reflected light 154, detector 138 generates an electrical signal E that represents the intensity of reflected light 154.

Any voltage between conductor 12 on the surface 14 of device under test 10 and voltage reference point 16 establishes an electric field that extends between conductor 12 and SPR transducer 120. Electro-optic transducer 110 is located in the electric field and is therefore subject to the electric field. The electric field changes the refractive index of electro-optic transducer 110. Surface plasmon resonance in SPR transducer 120 converts the change in the refractive index of electro-optic transducer 110 to a change in the reflectivity of SPR transducer 120 and, hence, a change in the intensity of reflected light 154. As will be described in detail below, the level of electrical signal E generated by detector 138 provides a measure of the voltage on conductor 12.

Figure 2:
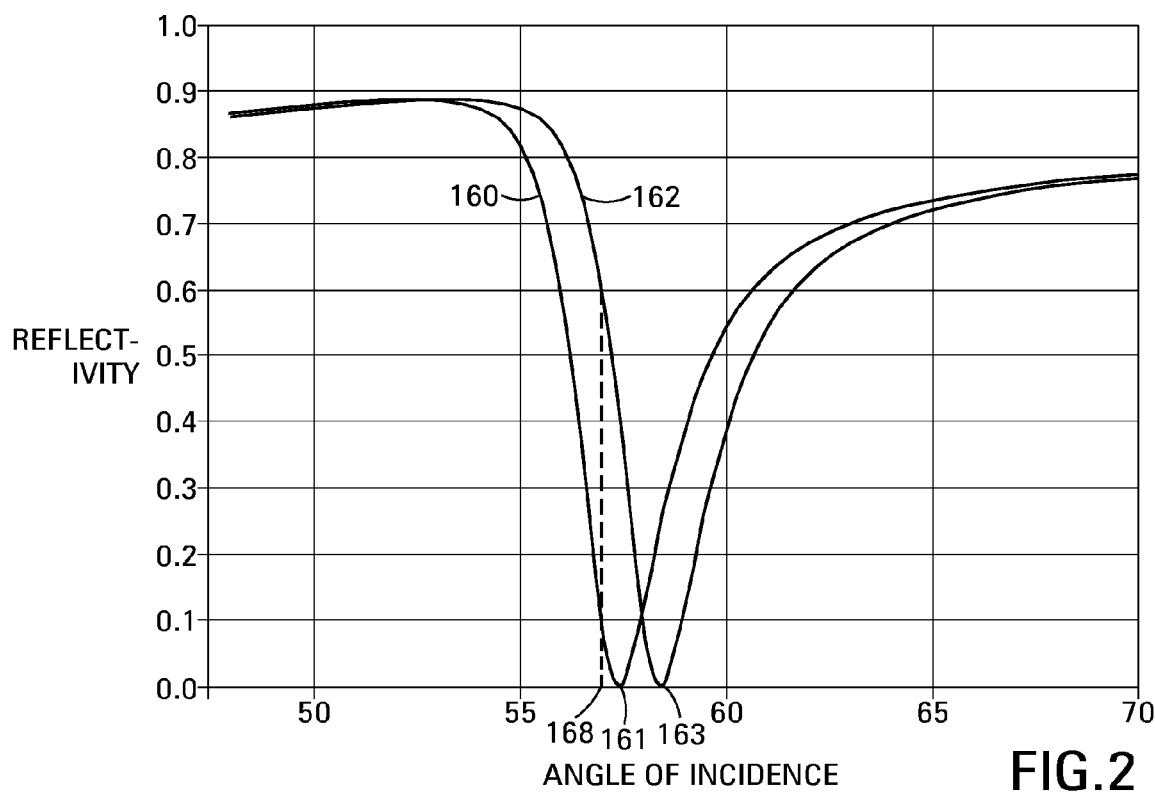
FIG. 2 is a graph showing the variation of reflectivity with angle of incidence θ at two different values of electric field in an example of the voltage sensor shown in FIG. 1.

FIG. 2 is a graph showing the variation of the reflectivity of SPR transducer 120 with angle of incidence θ on SPR transducer 120. Referring additionally to FIG. 1, in FIG. 2, curve 160 shows the variation of reflectivity of SPR transducer 120 with angle of incidence when electro-optic transducer 110 is subject to no electric field. In the example shown, the reflectivity of SPR transducer 120 exhibits a minimum at an angle of incidence of approximately 57.5 degrees. Thus, when electro-optic transducer 110 is subject to no electric field, SPR transducer 120 has an SPR angle 161 of approximately 57.5 degrees. If laser 132 is positioned such that angle of incidence θ is equal to SPR angle 161, the intensity of reflected light 154 will be zero or close thereto.

Curve 162 shows the variation of reflectivity of SPR transducer 120 with angle of incidence θ on SPR transducer 120 when electro-optic transducer 110 is subject to an electric field. In the example shown, the liquid crystal material of electro-optic transducer 110 is one that increases in refractive index when subject to an electric field. The increased refractive index of electro-optic transducer 110 in turn increases the SPR angle of SPR transducer 120. In the example shown, when electro-optic transducer 110 is subject to an electric field, SPR transducer 120 has an SPR angle 163 about one degree greater than SPR angle 161.

It can be seen from FIG. 2 that curves 160 and 162 each have portions at angles of incidence θ greater than or less than the respective SPR angle 161, 163 where the reflectivity changes steeply with change of SPR angle. Such steeply-changing portions mean that only relatively small changes in the refractive index of electro-optic transducer 110 are needed to provide a measurable change in reflectivity. FIG. 2 shows an example in which laser 132 is positioned to illuminate SPR transducer 120 at an angle of incidence 168 of about 57 degrees. When electro-optic transducer 110 is not subject to an electric field, SPR transducer 120 has an SPR angle 161 and a reflectivity of about 0.1, whereas, when electro-optic transducer 110 is subject to the electric field, SPR transducer 120 has an SPR angle 163 and a reflectivity of about 0.6. Smaller voltages on conductor 12 generate smaller electric fields and correspondingly smaller changes in reflectivity.

In many applications, a meaningful test result can be obtained when the voltage measurement performed using voltage sensor 100 simply determines whether a voltage is present at the measurement location with which voltage sensor 100 is aligned in the x-y plane. Such a determination can be made simply by determining whether signal E generated by detector 138 is greater than or less than a threshold. In the example shown in FIG. 2, signal E increases in level when a voltage is present as the electric field due to the voltage causes the reflectivity characteristics of SPR transducer 120 to change from curve 160 to curve 162. More precise voltage measurements can be made by performing a calibration process in which the level of signal E generated by detector 138 is measured with known voltages at the measurement location and a known gap 112 (FIG. 1) between electro-optic transducer 110 and device under test 10. The size of gap 112 is taken into account in determining the voltage because the electric field to which electro-optic transducer 110 is subject depends not only on the voltage at the measurement location but also on gap 112. Strictly speaking, when electrical connection 18 is made to the SPR layer 182 of SPR transducer 120, the electric field depends on the z-direction distance between the measurement location and SPR layer 182. Voltage measurements having a resolution of the order of 100 mV are possible.

Figure 3:
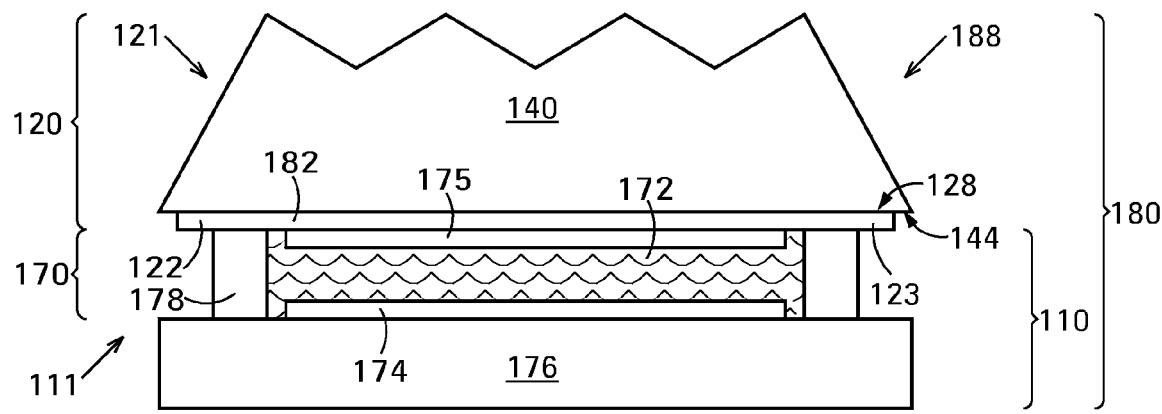
FIG. 3 is a side view showing details of part of a first example of a transducer assembly that may constitute part of a voltage sensor in accordance with an embodiment of the invention.

FIG. 3 is a side view showing details of part of first example 188 of a transducer assembly 180 that constitutes part of voltage sensor 100. Transducer assembly 180 is composed of an example 111 of electro-optic transducer 110 and an example 121 of SPR transducer 120. SPR transducer 121 is composed of an example 123 of resonant layer structure 122 and prism 140. Resonant layer structure 123 is deposited on the face 144 of prism 140, and is composed of SPR layer 182. SPR layer 182 is composed of a single, thin layer of metal, two or more thin layers of different metal metals or two or more thin layers of metal and dielectric, as described above. In an example of SPR transducer 121, SPR layer 182 was a single 45 nm-thick layer of gold deposited on the face 144 of prism 140.

Electro-optic transducer 111 is implemented as a liquid crystal cell 170 composed of liquid crystal material 172 sandwiched between orientation layers 174 and 175 that collectively define the crystal orientation of the liquid crystal material. Orientation layer 174 is deposited on a planar substrate 176 and orientation layer 175 is deposited on the resonant layer structure 123 of SPR transducer 121. Substrate 176 is mounted on SPR transducer 121 and is separated therefrom by a spacer 178. Prism 140, substrate 176 and spacer 178 collectively define a cavity in which liquid crystal material 172 is located. In an example of electro-optic transducer 111, spacer 178 had a thickness of 15 μm, orientation layers 174 and 175 were each a 40 nm-thick layer of polyimide and substrate 176 was a 160 μm-thick glass slide. Examples of materials that may be used as substrate 176 include ceramic, sapphire, silicon and a plastic such as polycarbonate. Substrate 176 of a material having a high dielectric constant gives voltage sensor 100 a greater voltage sensitivity than one of a material having a low dielectric constant.

Some the liquid crystal materials used as liquid crystal material 172 require the application of an electric field greater than a threshold electric field before the orientation of the crystals, and, hence, the refractive index of electro-optic transducer 110, starts to change. In such liquid crystal materials, the relationship between the change in orientation of the crystals and the applied electric field resembles the B-H curve of a ferromagnetic material. Thus, depending on the liquid crystal material, a voltage less than the voltage that produces an electric field greater than the threshold electric field may go unmeasured. Referring additionally to FIG. 1, this problem can be overcome by connecting a bias voltage source (not shown) in series with the electrical connection 18 between SPR sensor 121 and the voltage reference point 16 of device under test 10. The bias voltage source generates a bias voltage that, together with a voltage of, for example, zero at the measurement location, subjects electro-optic transducer 110 to an electric field greater than the threshold electric field. With such bias voltage applied, the refractive index of electro-optic transducer 110 will respond relatively linearly to a change in the electric field caused by the voltage at the measurement location being different from zero.

Figure 4:
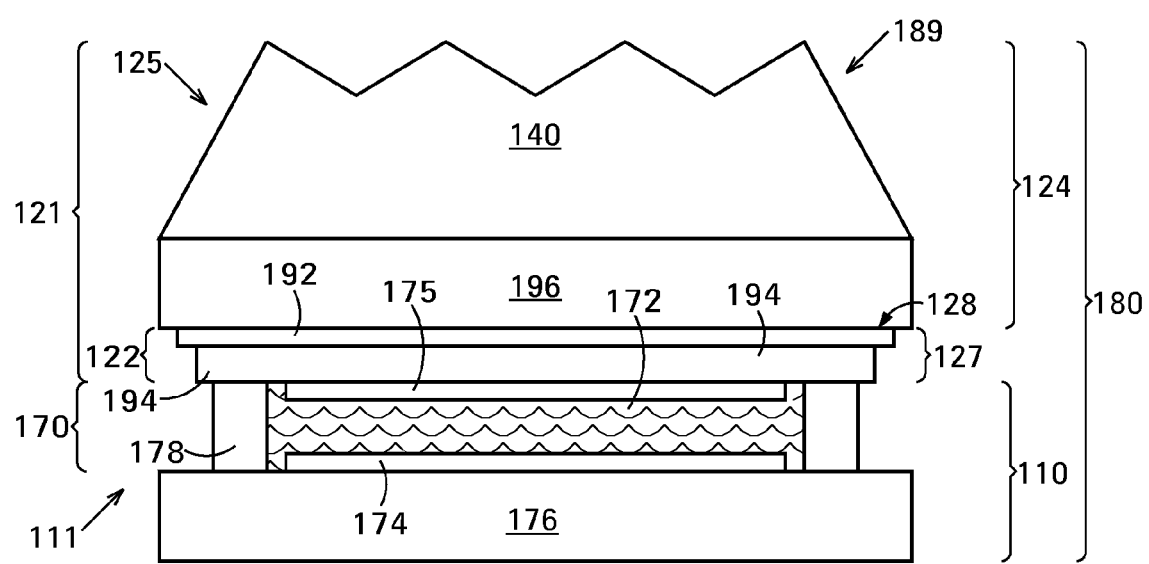
FIG. 4 is a side view showing details of part of a second example of a transducer assembly that may constitute part of a voltage sensor in accordance with an embodiment of the invention.

FIG. 4 is a side view showing part of a second example 189 of transducer assembly 180 that constitutes part of voltage sensor 100. Transducer assembly 189 is composed of electro-optic transducer 111 and another example 125 of surface plasmon resonance (SPR) transducer 120. Transducer assembly 189 has a greater voltage sensitivity and is more convenient to fabricate than transducer assembly 188 described above with reference to FIG. 3.

The example of SPR transducer 125 shown in FIG. 4 is composed of a resonant layer structure 127, a transparent, planar substrate 196 and prism 140. Planar substrate 196 and prism 140 collectively constitute transparent body 124 through which incident light 152 (FIG. 1) illuminates resonant layer structure 127.

Resonant layer structure 127 is composed of an SPR layer 192 and a substantially thicker dielectric layer 194. SPR layer 192 is composed of one or more thin layers of metal, having a thickness of the order of tens of nanometers, or two or more thin layers of metal and dielectric, as described above. SPR layer 192 is deposited on substrate 196 and is illuminated through prism 140 and substrate 196 by incident light 152 (FIG. 1). Dielectric layer 194 is juxtaposed with the surface of SPR layer 192 remote from substrate 196.

Resonant layer structure 127 is fabricated by depositing SPR layer 192 on a major surface of transparent substrate 196 and then depositing dielectric layer 194 on the exposed surface of SPR layer 192. The orientation layer 175 of liquid crystal cell 170 is then deposited on the exposed surface of dielectric layer 194 and is then suitably textured to provide its orientation function.

In an example of SPR transducer 125, SPR layer 192 was a single 40 nm-thick layer of gold, dielectric layer 194 was a 320 nm-thick layer of silicon nitride, and substrate 196 was 1 mm-thick glass slide. SPR layer 192 may be composed of a single layer of a metal other than gold, layers of more than one metal, or layers of metal and dielectric, as described above.

Examples of other dielectric materials that may be used as dielectric layer 194 are silicon dioxide ($SiO_2$), titanium dioxide ($TiO_2$), magnesium fluoride ($MgF_2$), aluminum oxide ($Al_2O_3$), lanthanum fluoride ($LaF_3$) and sodium aluminum fluoride (cryolite) ($Na_3AlF_6$). Example of other materials that may be used for substrate 196 are sapphire and a plastic such as polycarbonate. The refractive index of substrate 196 should be similar to that of prism 140 to minimize reflection at the interface between these elements. Reflection is minimized with identical refractive indices. SPR transducer 125 is simpler and less expensive to fabricate than SPR transducer 121 shown in FIG. 3 because planar substrate 196 on which resonant layer structure 127 is fabricated is more compatible with conventional fabrication processes than prism 140. Moreover, substrate 196 is less expensive than prism 140 and can more affordably be discarded in the event of a processing failure.

Electro-optic transducer 111 is implemented as liquid crystal cell 170 described above with reference to FIG. 3. Liquid crystal cell 170 is fabricated by depositing orientation layer 174 on substrate 176 and texturing the orientation layer. Spacer 178 is then attached to substrate 176. Spacer 178 is then attached to substrate 196. The cavity collectively defined by substrate 176, spacer 178 and substrate 196 is then filled with liquid crystal material 172.

The sub-assembly composed of electro-optic transducer 111, resonant layer structure 127 and substrate 196 is then mounted on prism 140 to complete the fabrication of transducer assembly 189. Substrate 196 is affixed to the face 144 of prism 140 such that it is interposed between resonant layer structure 127 and face 144. In an example, substrate 196 is affixed to face 144 using an index-matching adhesive to minimize reflections at the interface.

Figure 5:
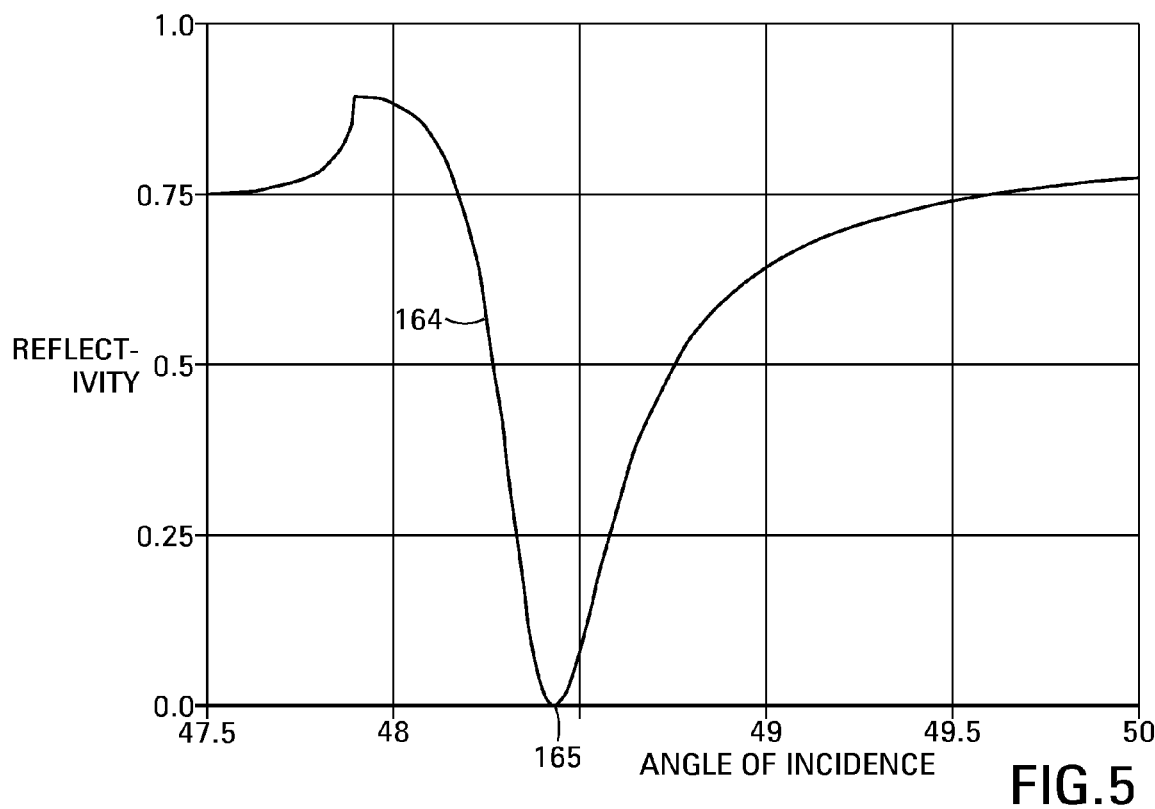
FIG. 5 is a graph showing the variation of reflectivity with angle of incidence θ in an example of the voltage sensor shown in FIG. 1 incorporating the transducer assembly shown in FIG. 4.

Dielectric layer 194 increases the voltage sensitivity of an example of voltage sensor 100 incorporating SPR transducer 125 relative to that of a voltage sensor incorporating SPR transducer 121 described above with reference to FIG. 3. The increase in voltage sensitivity is due to dielectric layer 194 increasing the quality factor Q of the resonance in resonant layer structure 127. FIG. 5 is a graph similar to the graphs shown in FIG. 2 in which curve 164 shows the variation of the reflectivity of the example of SPR transducer 125 shown in FIG. 4 with angle of incidence θ (FIG. 1). Curve 164 is similar in shape to curves 160 and 162 shown in FIG. 2. The reflectivity of SPR transducer 125 changes from 0.1 to 0.6 over a portion of curve 164. However, this change in reflectivity corresponds to a change in angle of incidence θ of about 0.2 degrees, whereas a similar change in reflectivity requires a change of about one degree in the angle of incidence in curves 160 and 162. Operationally, this amounts to about a five-fold increase in effective sensitivity. The surface plasmon resonance in SPR layer 192 is relatively lossy, and therefore has a relatively low Q. In contrast, dielectric layer 194 has an electromagnetic resonance with lower losses and therefore with a higher Q. Dielectric layer 194 is loosely coupled to SPR layer 192. Consequently, the low-Q surface plasmon resonance in SPR layer 192 excites but does not load the higher-Q electromagnetic resonance in dielectric layer 194.

The increased voltage sensitivity of an example of voltage sensor 100 incorporating SPR transducer 125 is obtained at the expense of a reduction in spatial resolution. In an example in which voltage sensor 100 incorporating SPR transducer 125 has a voltage sensitivity six times greater than that of voltage sensor 100 incorporating SPR transducer 121 described above with reference to FIG. 3, the spatial resolution of the voltage sensor incorporating SPR transducer 125 was about 100 µm, compared with about 30 µm for the voltage sensor incorporating SPR transducer 121.

In applications in which the increase of voltage sensitivity provided by dielectric layer 194 is not needed, but the greater convenience of fabrication of SPR transducer 125 is desirable, dielectric layer 194 may be omitted from transducer assembly 189.

Referring again to FIG. 1, voltage sensor 100 additionally comprises an armature (not shown) or another suitable mechanical structure on which optical system 130 and transducer assembly 180 are mounted. The armature locates and orientates laser 132 and auxiliary lens 134 relative to transducer assembly 180 such that incident light 152 illuminates location 126 on the surface 128 of SPR transducer 120 at an angle of incidence that induces surface plasmon resonance in SPR transducer 120. As noted above, this angle of incidence is typically greater than or less than the SPR angle of SPR transducer 120 for the wavelength of incident light 152 generated by laser 132, as described above with reference to FIGS. 2 and 5. The armature additionally locates and orients auxiliary lens 136 and detector 138 such that detector 138 receives reflected light 154 reflected by SPR transducer 120.

In some applications, voltage sensor 100 constitutes part of a test system (not shown) that comprises a test jig and an X-Y stage. Device under test 10 is mounted in the test jig for testing, and voltage sensor 100 is mounted on the X-Y stage. The X-Y stage moves voltage sensor 100 in a plane parallel to major surface 14 of device under test 10 and is capable of moving the voltage sensor to any measurement location on major surface 14 where a voltage is to be measured. Voltage sensor 100 is mounted on the X-Y stage to maintain the gap 112 between electro-optic transducer 110 and device under test 10 sufficiently large to prevent electro-optic transducer 110 from colliding with device under test 10 as voltage sensor 100 is moved. In some embodiments, the stage is an X-Y-Z stage capable of aligning voltage sensor 100 with each measurement location on device under test 10 in the x-y plane, and additionally capable of setting the gap 112 between electro-optic transducer 110 and device under test 10 to a predetermined value despite major surface 14 not being perfectly flat. Setting gap 112 to such predetermined value at each measurement location, or for a number of closely-spaced measurement locations, allows voltage sensor 100 to make more precise voltage measurements, and ensures that any calibration applied to voltage sensor 100 is valid at all measurement locations.

The examples of voltage sensor 100 described above with reference to FIGS. 1, 3 and 4 perform a single voltage measurement at each measurement location in device under test 10. After making a voltage measurement at one measurement location, the voltage sensor is moved to the next measurement location where it makes another voltage measurement. Voltage sensor 100 is therefore useful when contactless voltage measurements are to be made at measurement locations that are separated on device under test 10 by distances greater than the dimensions of transducer assembly 180 in the x-y plane. Other applications require that contactless voltage measurements be made at measurement locations that are separated by distances less than the dimensions of transducer assembly 180 in the x-y plane. Voltage sensor 100 can also be used for this purpose. However, the time needed to move voltage sensor 100 from one measurement location to the next may not be negligible. In such applications, an ability to make simultaneous contactless voltage measurements at such measurement locations would significantly reduce the time needed to perform the measurements, and, hence, the cost of testing device under test 10.

Figure 6:
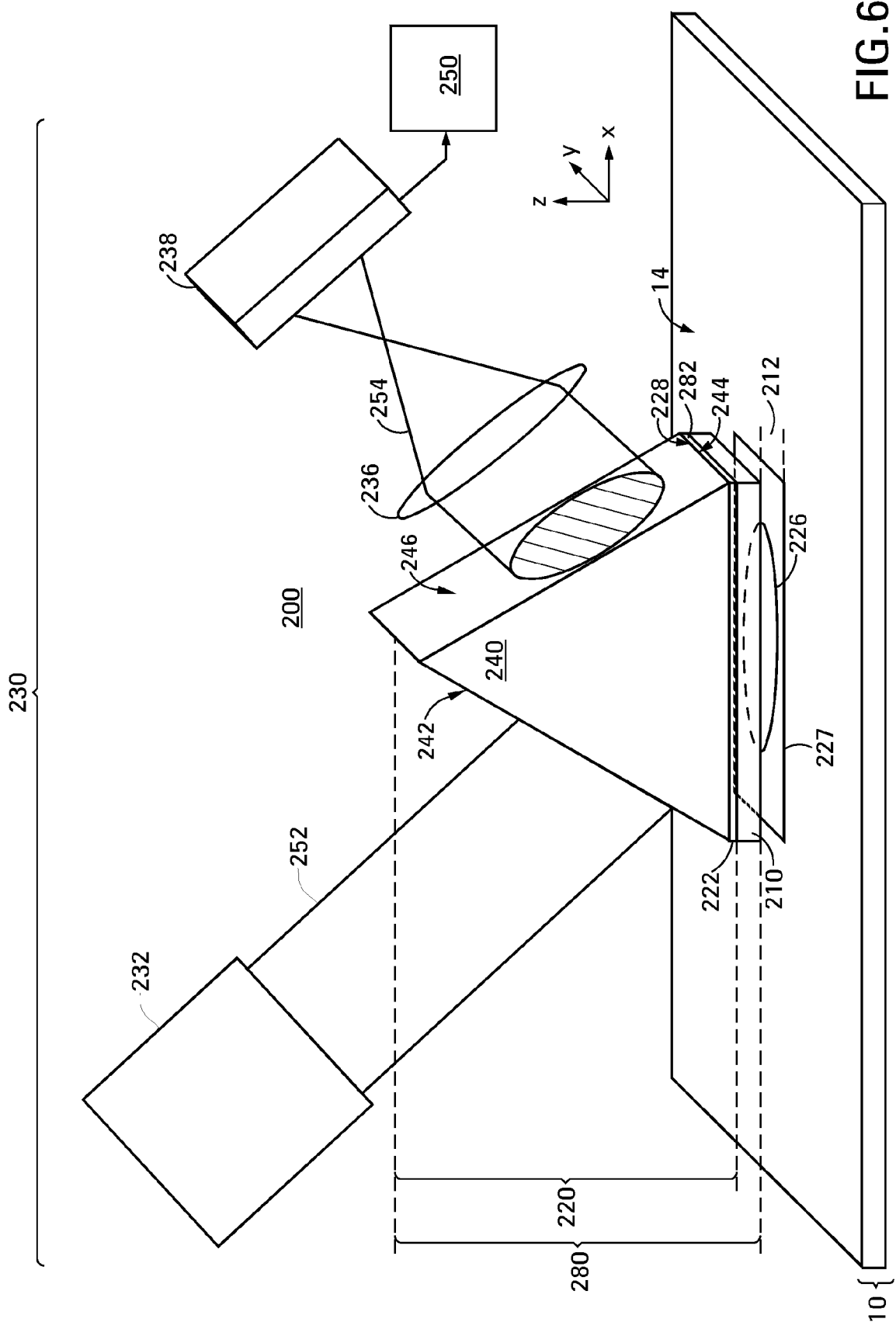
FIG. 6 is a schematic diagram showing an isometric view of another example of a voltage sensor in accordance with an embodiment of the invention.

FIG. 6 is a schematic diagram showing an isometric view of an example of a voltage sensor 200 in accordance with an embodiment of the invention. Voltage sensor 200 is capable of performing simultaneous contactless voltage measurements at measurement locations separated by distances less than the dimensions of the transducer assembly of the voltage sensor in a plane parallel to the major surface of the device under test. Voltage sensor 200 can be used, for example, to test the function of the switching transistor in each pixel in a region of a flat-panel display. In such a flat-panel display, the pixels have a pitch of about 250 µm. Elements of voltage sensor 200 that correspond to elements of voltage sensor 100 described above with reference to FIGS. 1, 3 and 4 are indicated using the same reference numerals with 100 added.

Voltage sensor 200 differs from voltage sensor 100 principally in the area of its transducers, the fraction of the area of its SPR transducer that is illuminated and the manner in which the light reflected by the SPR transducer is detected. Specifically, in voltage sensor 200, the transducers are typically larger in area those of voltage sensor 100, a majority of the area of the SPR transducer is illuminated instead of the small spot illuminated in voltage sensor 100, and the light reflected by the SPR transducer is focused on an array of light detectors instead of on an single light detector. Focusing the light reflected by the SPR transducer on an array of light detectors allows the reflectivity of the SPR transducer to be measured at as many locations on the SPR transducer as there are detectors in the array of light detectors and, hence, for voltage sensor 200 to make simultaneous voltage measurements at a corresponding number of measurement locations on the device under test.

Typically, a pixellated light detector is used to provide the array of light detectors. An array of discrete light detectors can alternatively be used. A pixellated light detector theoretically allows the reflectivity of the SPR transducer, and, hence, a voltage, to be measured at as many locations on the SPR transducer as there are pixels in the pixellated light detector.

Voltage sensor 200 is composed of an electro-optic transducer 210, an SPR transducer 220 and an optical system 230. Electro-optic transducer 210 is operable to translate a spatial variation in an electric field dependent on voltages in device under test 10 to a spatial variation in its refractive index. SPR transducer 220 is juxtaposed with electro-optic transducer 210, and is operable to translate the spatial variation in the refractive index of electro-optic transducer 210 to a spatial variation in its reflectivity. Optical system 230 comprises a pixellated light detector 238 that provides an array of light detectors, and is configured to illuminate a region of SPR transducer 220 with incident light at a surface plasmon resonance-inducing angle of incidence and to focus light reflected by the SPR transducer on pixellated light detector 238.

Electro-optic transducer 210 is similar to electro-optic transducer 110 described above with reference to FIGS. 1, 3 and 4 and will therefore not be described in detail again. Electro-optic transducer 210 differs from electro-optic transducer 110 in that it is typically, but not necessarily, larger in area in the x-y plane than electro-optic transducer 110.

SPR transducer 220 is similar to SPR transducer 120 described above with reference to FIGS. 1, 3 and 4 and will therefore not be described in detail again. Again, SPR transducer 220 differs from SPR transducer 120 in that it is typically, but not necessarily, larger in area in the x-y plane than SPR transducer 120. The overlap in area in the x-y plane between electro-optic transducer 210 and SPR transducer 220 defines the extent of a region of device under test 10 within which voltage sensor 200 can perform simultaneous voltage measurements.

In the example shown, SPR transducer 220 is composed of a resonant layer structure 222 and a prism 240. In this example, resonant layer structure 222 is composed of SPR layer 282 deposited on a face 244 of prism 240 in a manner similar to that of resonant layer structure 122 described above with reference to FIG. 3. Electro-optic transducer 210 is composed of a liquid crystal cell similar to liquid crystal cell 170 described above with reference to FIG. 3. A transducer assembly 280 composed of electro-optic transducer 210 and SPR transducer 220 is fabricated by depositing resonant layer structure 222 on the face 244 of prism 240. Some of the layers constituting electro-optic transducer 210 are deposited on resonant layer structure 222 in a manner similar to that described above with reference to FIG. 3. The remaining layers constituting electro-optic transducer 210 are deposited on a planar substrate (not shown) similar to substrate 176 (FIG. 3) that is then mounted on face 244 of prism 240 by a spacer (not shown), also as described above with reference to FIG. 3. Alternatively, part of SPR transducer 220 and part of electro-optic transducer 210 are constructed on the surface of a planar substrate (not shown) similar to substrate 196 (FIG. 4) in a manner similar to that in the example 189 of transducer assembly 180 described above with reference to FIG. 4. The substrate is then affixed to face 244 of prism 240 as described above. In addition to SPR layer 282, resonant layer structure 222 may include a dielectric layer similar to dielectric layer 194 described above with reference to FIG. 4.

Optical system 230 is composed of a light source 232, an imaging lens 236 and pixellated light detector 238. Voltage sensor 200 additionally comprises an armature (not shown) or another suitable mechanical structure on which light source 232, transducer assembly 280, imaging lens 236 and pixellated light detector 238 are mounted.

Light source 232 is composed of a laser or LED and one or more lenses (not shown) that collimate the light generated by the laser or LED to a broad beam of light and direct such beam of light towards face 244 of prism 240 as incident light 252. The armature (not shown) locates and orientates light source 232 relative to prism 240 such that, after passing through prism 240, incident light 252 illuminates the surface 228 of SPR transducer 220 at an angle of incidence that induces surface plasmon resonance in SPR transducer 220, i.e., in SPR layer 282. As noted above, the angle of incidence at which surface 228 is illuminated is typically greater than or less than the SPR angle of SPR transducer 220 for the wavelength of the incident light generated by light source 232, as described above with reference to FIGS. 2 and 5.

The light beam that provides incident light 252 has a cross-sectional shape and area such that it illuminates many points, i.e., a region, on the surface 228 of SPR transducer 220, in contrast to the single point illuminated by optical system 130 described above with reference to FIG. 1. In a practical example, optical system 230 illuminates a non-point region of surface 228; for example, a majority of the area of surface 228. In the example shown, the light beam has a circular cross section and illuminates an elliptical region on surface 228. The footprint of the illuminated region of surface 228 projected in a geometric sense onto the major surface 14 of device under test 10 is shown at 226. In other examples, the cross-sectional area of the light beam is shaped such that the light beam illuminates all of surface 228 with a substantially uniform intensity. The footprint of the entire surface 228 projected in a geometric sense onto the major surface 14 of device under test 10 is shown at 227. Footprints 226 and 227 corresponding to respective exemplary illuminated regions of the surface 228 of SPR transducer 220 represent respective active regions in which voltage sensor 200 is capable of making voltage measurements.

The surface 228 of SPR transducer 220 reflects incident light 252 as reflected light 254. SPR transducer 220 has a reflectivity that depends on the refractive index of electro-optic transducer 210. The armature (not shown) additionally locates and orients imaging lens 236 and pixellated light detector 238 such that imaging lens 236 receives reflected light 254 reflected by SPR transducer 220.

Imaging lens 236 forms an image from reflected light 254 on the surface of pixellated light detector 238. Imaging lens 236 may be composed of more than one lens. Digital camera modules are commercially available and one may be used instead of imaging lens 236 and pixellated light detector 238. Such digital camera module may be used on its own or together with one or more additional lenses. Better results are obtained with digital camera modules from which the color mosaic filter has been omitted or removed.

The illuminated region of the surface 228 of SPR transducer 220 appears in the image of surface 228 formed by imaging lens 236 on pixellated light detector 238. In the absence of voltages in the portion of device under test 10 aligned with voltage sensor 200, the image of surface 228 is substantially uniform in brightness. When the device under test is exercised in a manner that applies voltages to measurement locations in the portion of device under test 10 aligned with voltage sensor 200, the reflectivity of portions of the surface 228 of SPR transducer 220 that are aligned in the x-y plane with the measurement locations will be greater or less than in the absence of voltage, as described above with reference to FIGS. 2 and 5. As a result, the portions of surface 228 aligned with the measurement locations will appear brighter or darker than the remainder of surface 228, and the image formed on pixellated light detector 238 will have corresponding spatial variations in brightness.

Pixellated light detector 238 operates in response to various clock and control signals (not shown) and the intensity of the image formed thereon to generate a signal E. Typically, pixellated light detector 238 comprises an analog-to-digital converter (not shown) that converts the analog signal generated by each pixel to a respective digital value, and signal E is composed of one digital value for each pixel of pixellated light detector 238. Each digital value represents the intensity of the reflected light falling on the respective pixel. Typically, the intensity-representing digital values are in raster-scan order in signal E. A blanking technique, such as that disclosed in U.S. Pat. No. 5,475,420, may be used to exclude from signal E digital values originating from pixels other than those on which the image of the illuminated region of surface 228 is formed. Alternatively, signal E may be an analog signal.

In the example shown in FIG. 6, signal E generated by pixellated light detector 238 is input to a signal processor 250 that derives from signal E a voltage measurement for each of the measurement locations in device under test 10 aligned with the active region of voltage sensor 200. In one example, all of device under test 10 fits within the active region of voltage sensor 200. In this case, processor 250 processes a single instance of signal E to obtain a voltage measurement for each measurement location in device under test 10. In another example, the active region of voltage sensor 200 is less than the area of device under test 10. In this case, voltage sensor 200 generates a respective instance of signal E for each of a number of different positions of voltage sensor 200 relative to device under test 10. The number of positions is sufficient to cover the entire area of device under test 10 in which measurement locations exist. Processor 250 then processes all the instances of signal E to generate a voltage measurement for each measurement location in device under test 10. Voltage sensor 200 is moved in the x-y plane relative to device under test 10 by an X-Y stage, for example, as described above.

In a given x-y position of voltage sensor 200 relative to device under test 10, a 1:1 relationship is assumed between the position of each measurement location in device under test 10 and a corresponding position on the surface 228 of SPR transducer 220. It is also assumed that the image of the portion of surface 228 corresponding to each measurement location falls on more than one respective pixel of pixellated light detector 238. Signal processor 250 is provided with the following information:

1. The position, or each position, of voltage sensor 200 relative to device under test 10.
2. For each position of voltage sensor 200 relative to device under test 10, the positions of the measurement locations in device under test 10.
3. The geometrical relationship between a position on the surface 228 of SPR transducer 220 and a corresponding position in the image of surface 228 formed on pixellated light detector 238, and, hence, the geometrical relationship between the position on surface 228 and the coordinates of one or more pixels of pixellated light detector 238.
4. The position in signal E of the digital value corresponding to each pixel of pixellated light detector 238.

Signal processor 250 operates in response to the above-described topological and positional relationship information to extract from each instance of signal E the digital values corresponding to the pixels of pixellated light detector 238 that receive light reflected by a portion of surface 228 whose reflectivity depends on the voltage at each measurement location in device under test 10 aligned with the active region of voltage sensor 200. For each measurement location, the respective digital values are combined to provide a representative digital value that represents the voltage at such measurement location. The digital values can be combined by such processing as adding, averaging, weighted averaging, determining a mean, determining a weighted mean, determining a median, determining a maximum, determining a minimum or another combining process appropriate to the application. The voltage at the respective measurement location is then determined from the representative digital value. As noted above, the voltage measurement derived from the representative digital value can range from one that simply indicates whether a voltage is present at the measurement location to one that provides a fairly precise quantification of the voltage at the measurement location. For example, a look-up table may be used to translate the representative digital value to a voltage. In some applications, signal processor 250 displays or outputs to an external device a voltage measurement for each measurement location. In other applications, the signal processor internally processes the voltage measurements to determine a pass/fail result for device under test 10.

In another example, signal processor 250 simply compares each instance of signal E with a corresponding example of signal E generated by voltage sensor 200, or a voltage sensor similar to voltage sensor 200, in response to a known good example of device under test 10. Signal processor 250 indicates whether any significant differences exist between the instance of signal E and the example of signal E, and optionally indicates a measurement location in the device under test corresponding to each such difference.

Voltage sensor 200 is shown in FIG. 6 positioned in the x- and y-directions to measure voltages at measurement locations in a region of exemplary device under test 10 corresponding to the active region 226 or 227 of the voltage sensor. Voltage sensor 200 is additionally positioned in the z-direction such that the surface of electro-optic transducer 210 remote from SPR transducer 220 is separated from the major surface 14 of device under test 10 by a narrow gap 212. As mentioned above, reducing gap 212 increases the spatial resolution and voltage sensitivity of voltage sensor 200. However, gap 212 should be sufficiently wide to ensure that voltage sensor 200 will not collide with high spots on device under test 10 as it is moved in the x- and y-directions to perform voltage measurements at multiple positions relative to device under test 10.

In an example of using voltage sensor 200 to verify the proper operation of the pixels in a region of the above-mentioned flat-panel display, each of the measurement locations corresponds to the electrode of a respective one of the pixels in the region of the display. Voltage sensor 200 is used to verify that the thin-film transistor that drives each electrode is capable of switching ON and OFF. In a mode of operation of voltage sensor 200 similar to the example described above with reference to FIG. 2, an electrode controlled by a thin-film transistor in its ON state will appear brighter than an electrode controlled by a thin-film transistor in an OFF state in the image formed on pixellated detector 238. In each position of voltage sensor 200 relative to the flat-panel display, the voltage sensor performs as few as two measurement operations (one performed with all the thin-film transistors ON, the other performed with all the thin-film transistors OFF) to verify proper operation of thousands of pixels.

In currently-envisaged examples of voltage sensor 200, the dimensions of face 244 of prism 240 are about 50 mm square. A prism of this size is a substantial contributor to the mass of voltage sensor 200. In applications in which the mass of voltage sensor 200 is important, such as those in which the voltage sensor is moved from position-to-position relative to device under test 10 at high speed, a thin, planar substrate of a material having a refractive index greater than that of air substrate can be used as transparent body 124 (FIG. 1) instead of a prism.

Figure 7:
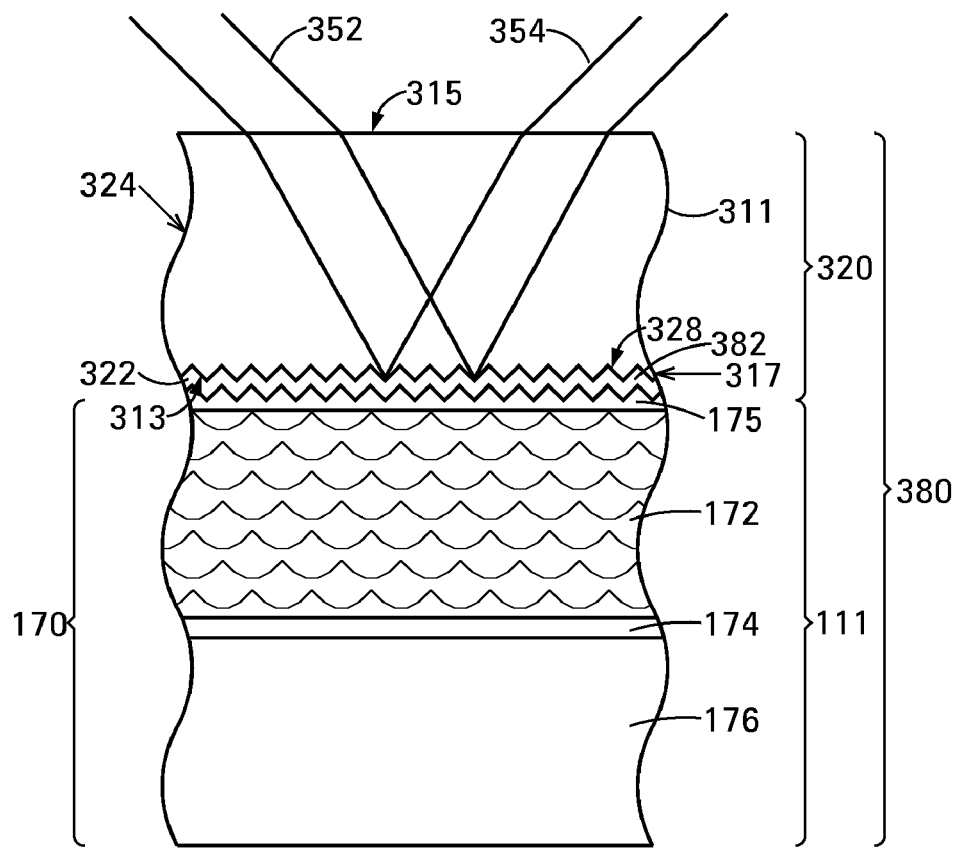
FIG. 7 is an enlarged side view showing details of part of a third example of a transducer assembly that may constitute part of a voltage sensor in accordance with an embodiment of the invention.

FIG. 7 is an enlarged side view showing part of a third example of a transducer assembly 380 that may constitute part of a voltage sensor in accordance with an embodiment of the invention. Transducer assembly 380 will be described with reference to an example suitable for incorporation in voltage sensor 100. Transducer assembly 380 may also be incorporated in voltage sensor 200. In transducer assembly 380, a thin, flat substrate, substantially cheaper and lower in mass than prism 140 (FIG. 1), provides a transparent body through which the SPR transducer is illuminated.

Referring briefly to FIG. 1, to match the wavelength of incident light 152 to the wavelength of the plasmons induced in SPR sensor 120, the incident light has to illuminate the surface 128 of SPR layer 182 through transparent body 124 and has to have a relatively large angle of incidence θ on surface 128. Transparent body 124 has a higher refractive index than air. To achieve a large angle of incidence within transparent body 124 notwithstanding refraction at the surface of the transparent body reducing the angle of incidence, the transparent body is shaped as triangular prism 140 in the example of SPR sensor 120 shown in FIG. 1. Incident light 152 is incident on face 142 of prism 140, passes through the prism and exits through surface 144 to illuminate resonant layer structure 122. The angle of face 142 relative to face 144 is similar to the desired angle of incidence θ of incident light 152 on face 144. As a result, the angle of incidence of incident light 152 on face 142 is small, so that refraction at face 142 negligibly decreases the angle of incidence θ of incident light 152 on face 144 and, hence, on the surface 128 of SPR layer 182.

Transducer assembly 380 is composed of electro-optic transducer 111 and an SPR transducer 320. SPR transducer 320 is composed of resonant layer structure 322 and a thin, planar substrate 311 that provides transparent body 324 through which incident light 352 illuminates resonant layer structure 322. Substrate 311 has a major surface 313 and a major surface 315. Resonant layer structure 322 is deposited on major surface 313. Major surface 315 is opposite major surface 313. Major surface 315 is illuminated by incident light 352, and reflected light 354 reflected by resonant layer structure 322 passes through major surface 315.

In the example shown, resonant layer structure 322 is composed of an SPR layer 382, and SPR layer 382 is a single layer of metal having a thickness of the order of tens of nanometers. In an example, SPR layer 382 was a single layer of gold about 45 nm thick. The alternative structures of SPR layer 182 described above with reference to FIGS. 1 and 3 may be applied to SPR layer 382. Resonant layer structure 322 may additionally comprise a layer of dielectric material similar to dielectric layer 194 described above with reference to FIG. 4.

Incident light 352 is incident on the surface 315 of substrate 311 at a substantially greater angle of incidence than the angle of incidence of incident light 152 on face 142 of prism 140. Incident light 352 is refracted at surface 315 so that its angle of incidence on surface 313 is less than that on surface 315. However, even if the angle of incidence on surface 315 were almost 90 degrees, at which angle of incidence the loss of incident light through reflection at surface 315 would be undesirably large, the angle of incidence on surface 313, and, hence on the surface of the SPR layer 382, would be too small to induce surface plasmon resonance in the SPR layer.

To enable incident light 352 to induce surface plasmon resonance in SPR layer 382 notwithstanding its smaller angle of incidence relative to incident light 152 (FIG. 1), SPR layer 382 has a corrugated surface 328. In the example shown, SPR layer 382 constituting resonant layer structure 322 is formed with corrugated surface 328 by defining a grating 317 in the surface 313 of substrate 311. Then, when SPR layer 382 is deposited on substrate 311, its surface 328 conforms to the contours of grating 317. When incident light 352 illuminates contoured surface 328, the distance between crests of the plasmon wavefronts induced in the contoured surface 328 is matched to the distance between the crests of the optical wavefronts in the direction of travel of incident light 352. Consequently, incident light 352 is capable of inducing surface plasmon resonance in the corrugated surface 328 of SPR layer 382 constituting resonant layer structure 322 despite its angle of incidence being less that that which would induce surface plasmon resonance in an otherwise-similar SPR layer having a non-corrugated surface. The angle of incidence, the wavelength of incident light 352, the properties of resonant layer structure 322 and the properties of grating 317 are selected such that, in the absence of an electric field, SPR transducer 320 has a reflectivity intermediate between its normal reflectivity and minimum reflectivity, as described above with reference to FIG. 2.

In the transducer assembly examples described above with reference to FIGS. 1, 3, 4, 6 and 7, the liquid crystal cell that constitutes the electro-optic transducer comprises a planar substrate (e.g., substrate 174 shown in FIG. 7). In operation of the voltage sensor that incorporates the transducer assembly, the planar substrate is interposed between the device under test and the resonant layer structure and the liquid crystal material of the voltage sensor. The thickness of the planar substrate defines a minimum distance between the device under test and the resonant layer structure and the liquid crystal material of the voltage sensor, hence, limits both the voltage sensitivity and the spatial resolution of the voltage sensor.

Figure 8:
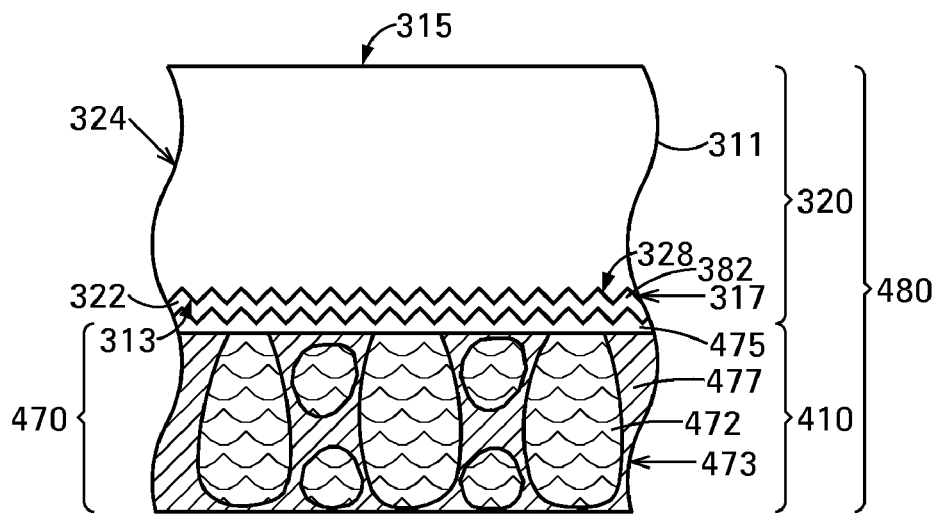
FIG. 8 is an enlarged side view showing details of part of a fourth example of a transducer assembly that may constitute part of a voltage sensor in accordance with an embodiment of the invention.

FIG. 8 is an enlarged side view showing part of a fourth example of a transducer assembly 480 that may constitute part of a voltage sensor in accordance with an embodiment of the invention. Transducer assembly 480 will be described with reference to an example suitable for incorporation in voltage sensor 100. Transducer assembly 480 may also be incorporated in voltage sensor 200. Transducer assembly 480 is composed of electro-optic transducer 410 and SPR transducer 320. SPR transducer 320 is described above with reference to FIG. 7 and will not be described again here. Any of the above-described SPR transducers may be substituted for SPR transducer 320 in transducer assembly 480. Electro-optic transducer 410 may be used as the electro-optic transducer in any of the above-described transducer assemblies.

Electro-optic transducer 410 is implemented as a liquid crystal cell 470 composed of a layer of polymer-dispersed liquid crystal material 473 juxtaposed with orientation layer 475. Polymer-dispersed liquid crystal material 473 is composed of liquid crystal material 472 dispersed in a solid matrix 477. Orientation layer 475 deposited on SPR transducer 320 defines the crystal orientation of those regions of the liquid crystal material that make contact with it. Solid matrix 477 is an epoxy or another suitable material. Techniques for fabricating polymer-dispersed liquid crystal material are known in the art and will therefore not be described here. In an example, layer 473 of polymer-dispersed liquid crystal material has a thickness of 10 μm and orientation layer 475 is a 40 nm-thick layer of polyimide.

Transducer assembly 480 lacks a substrate similar to substrate 176 (FIG. 7) interposed between liquid crystal material 472 and the device under test. Thus, in a voltage sensor incorporating transducer assembly 480, liquid crystal material 472 and resonant layer structure 322 can be located closer to the device under test than the liquid crystal material and resonant layer structure of a voltage sensor whose transducer assembly incorporates a substrate similar to substrate 176. A voltage sensor that incorporates transducer assembly 480 therefore has a better voltage sensitivity and spatial resolution than a voltage sensor whose electro-optic transducer has a substrate interposed between the liquid crystal material and the device under test.

This disclosure describes the invention in detail using illustrative embodiments. However, the invention defined by the appended claims is not limited to the precise embodiments described.

I claim:

1. A voltage sensor capable of contactless voltage measurement in a device-under-test, the voltage sensor comprising:
an electro-optic transducer comprising a layer of crystal material, the electro-optic transducer operable to translate an electric field dependent on the voltage in the device under test to a variation in refractive index;
a surface plasmon resonance (SPR) transducer juxtaposed with the electro-optic transducer, the SPR transducer operable to translate the variation in the refractive index of the electro-optic transducer to a variation in reflectivity; and
an optical system configured to illuminate the SPR transducer with incident light at a surface plasmon resonance-inducing angle of incidence and to detect light reflected by the SPR transducer.

2. The voltage sensor of claim 1, in which:
the electro-optic transducer additionally comprises a planar substrate; and
the layer of liquid crystal material is sandwiched between the SPR transducer and the planar substrate.

3. The voltage sensor of claim 1, in which the electro-optic transducer comprises a layer of polymer-dispersed liquid crystal material.

4. The voltage sensor of claim 1, in which the SPR transducer comprises:
a resonant layer structure; and
a transparent body through which the optical system illuminates the resonant layer structure.

5. The voltage sensor of claim 4, in which a single SPR layer constitutes the resonant layer structure.

6. The voltage sensor of claim 5, in which the SPR layer comprises a single layer of metal having a thickness of the order of tens of nanometers.

7. The voltage sensor of claim 5, in which the resonant layer structure additionally comprises a layer of dielectric material between the SPR layer and the electro-optic transducer.

8. The voltage sensor of claim 4, in which the SPR layer comprises layers of different materials.

9. The voltage sensor of claim 4, in which:
the transparent body comprises a prism;
the resonant layer structure is deposited on a face of the prism; and
the optical system is configured to illuminate another face of the prism.

10. The voltage sensor of claim 4, in which:
the transparent body comprises:
a prism, and
a planar substrate on which the resonant layer structure is deposited, the planar substrate attached to a face of the prism with the substrate interposed between the resonant layer structure and the prism; and
the optical system is configured to illuminate another face of the prism.

11. The voltage sensor of claim 4, in which:
the transparent body comprises a planar substrate having a first major surface and a second major surface opposite the first major surface;
the resonant layer structure comprises an SPR layer having a corrugated surface facing the first major surface of the substrate; and
the optical system is configured to illuminate the second major surface of the substrate.

12. The voltage sensor of claim 11, in which:
the planar substrate comprises a grating in the first major surface; and
the SPR layer is deposited on the grating.

13. The voltage sensor of claim 4, in which the SPR transducer is electrically connected to a reference potential.

14. The voltage sensor of claim 1, in which the optical system is configured to illuminate a point on the SPR transducer and comprises no more than one light detector arranged to receive the light reflected by the SPR transducer.

15. The voltage sensor of claim 1, in which the optical system is configured to illuminate at least a region of the SPR transducer and comprises:
an array of light detectors; and
an imaging element arranged to receive the light reflected by the SPR transducer and operable to form an image on the array of light detectors therewith.

16. A voltage sensor capable of contactlessly mapping a spatial voltage variation in a device under test, the voltage sensor comprising:
an electro-optic transducer comprising liquid crystal material, the electro-optic transducer operable to translate a spatial variation in an electric field dependent on the spatial voltage variation in the device under test to a corresponding spatial variation in refractive index;
a surface plasmon resonance (SPR) transducer juxtaposed with the electro-optic transducer and operable to translate the spatial variation in the refractive index of the electro-optic transducer to a corresponding spatial variation in reflectivity; and
an optical system comprising a pixellated light detector, the optical system configured to illuminate the SPR transducer in a region aligned with a region of the device under test in which at least part of the spatial voltage variation occurs, the optical system configured to form an image on the pixellated light detector using the light reflected by the SPR transducer and spatially modulated by the spatial variation in the reflectivity thereof.

17. The voltage sensor of claim 16, in which the SPR transducer comprises:
a resonant layer structure; and
a transparent body through which the optical system illuminates the resonant layer structure.

18. The voltage sensor of claim 17, in which:
the transparent body comprises a planar substrate; and
the resonant layer structure comprises an SPR layer having a corrugated surface juxtaposed with the planar substrate.

* * * * *

UNITED STATES PATENT AND TRADEMARK OFFICE
CERTIFICATE OF CORRECTION

PATENT NO. : 7,474,404 B2  Page 1 of 1
APPLICATION NO. : 11/741567
DATED : January 6, 2009
INVENTOR(S) : VanWiggeren It is certified that error appears in the above-identified patent and that said Letters Patent is hereby corrected as shown below:

In column 18, line 55, in Claim 1, delete "of" and insert -- of liquid --, therefor.

Signed and Sealed this

Fourteenth Day of July, 2009

JOHN DOLL
*Acting Director of the United States Patent and Trademark Office*